United States Patent
Sah

(10) Patent No.: US 12,059,403 B2
(45) Date of Patent: Aug. 13, 2024

(54) USE OF SWELL1 INHIBITORS AND MODULATORS TO TREAT TYPE 2 DIABETES AND OBESITY

(71) Applicant: UNIVERSITY OF IOWA RESEARCH FOUNDATION, Iowa City, IA (US)

(72) Inventor: Rajan Sah, Iowa City, IA (US)

(73) Assignee: UNIVERSITY OF IOWA RESEARCH FOUNDATION, Iowa City, IA (US)

(*) Notice: Subject to any disclaimer, the term of this patent is extended or adjusted under 35 U.S.C. 154(b) by 283 days.

(21) Appl. No.: 16/322,709

(22) PCT Filed: Aug. 4, 2017

(86) PCT No.: PCT/US2017/045582
§ 371 (c)(1),
(2) Date: Feb. 1, 2019

(87) PCT Pub. No.: WO2018/027175
PCT Pub. Date: Feb. 8, 2018

(65) Prior Publication Data
US 2021/0369670 A1    Dec. 2, 2021

Related U.S. Application Data

(60) Provisional application No. 62/489,265, filed on Apr. 24, 2017, provisional application No. 62/371,061, filed on Aug. 4, 2016.

(51) Int. Cl.
| A61K 31/192 | (2006.01) |
| A61K 31/138 | (2006.01) |
| A61K 31/40  | (2006.01) |
| A61P 3/08   | (2006.01) |

(52) U.S. Cl.
CPC ........... *A61K 31/40* (2013.01); *A61K 31/138* (2013.01); *A61K 31/192* (2013.01)

(58) Field of Classification Search
CPC .... A61K 31/192; A61K 31/40; A61K 31/138; A61P 3/08; A61P 3/10
See application file for complete search history.

(56) References Cited

U.S. PATENT DOCUMENTS

| 2,914,563 A | 11/1959 | Allen et al. |
| 3,274,213 A | 9/1966 | Daniel |
| 4,465,850 A | 8/1984 | Cragoe et al. |
| 4,536,516 A | 8/1985 | Harper et al. |
| 5,567,713 A * | 10/1996 | Cullinan ............ A61K 31/35 514/324 |
| 2009/0099265 A1 * | 4/2009 | van As ................ A61P 3/08 514/651 |
| 2009/0304714 A1 | 12/2009 | Saltiel et al. |
| 2012/0208836 A1 | 8/2012 | Saltiel et al. |
| 2015/0125433 A1 | 5/2015 | Hornstein et al. |
| 2015/0250802 A1 | 9/2015 | Labrie et al. |
| 2015/0253303 A1 | 9/2015 | Jentsch et al. |

FOREIGN PATENT DOCUMENTS

| EP | 0047011 B1 | 6/1985 |
| EP | 2919009 A1 | 9/2015 |
| GB | 1013907 A | 12/1965 |
| WO | 2013102207 A1 | 7/2013 |
| WO | 2016029191 A2 | 2/2016 |

OTHER PUBLICATIONS

Figueroa et al. Channels 2022, 16 (1), 27-36.*
Ben-Or Frank, M, et al., "Effects of accumulation of lipid droplets on load transfer between and within adipocytes", Biomechanics and Modeling Mechanobiology 14(1), 15-28 (2014).
Best, L, et al., "Inhibition of glucose-induced electrical activity in rat pancreatic β-cells by DCPIB, a selective inhibitor of volume-sensitive anion currents", Eur J Pharmacol 489, 13-19 (2004).
Bourke, R, et al., "Adenosine-stimulated astroglial swelling in cat cerebral cortex in vivo with total inhibition by a hon-diuretic acylaryloxyacid derivative", J Neurosurg 55, 364-370 (1981).
Decher, N, et al., "DCPIB is a novel selective blocker of I(CI,swell) and prevents swelling-induced shortening of guinea pig atrial action potential duration", Br J Pharmacol 134, 1467 (2001).
Farnier, C, et al., "Adipocyte functions are modulated by cell size change: potential involvement of an integrin/ERK signalling pathway", Int J Obes Relat Metab Disord 27(10), 1178-1186 (2003).
Hayashi, T, et al., "Factor for adipocyte differentiation 158 gene disruption prevents the body weight gain and insulin resistance induced by a high-fat diet", Biol Pharm Bull 34(8), 1257-1263 (2011).
Heinonen, S, et al., "Adipocyte morphology and implications for metabolic derangements in acquired obesity", Int J Obes 38(1), 1423-1431 (2014).
Kang, et al., "SWELL1 is a glucose sensor regulating β-cell excitability and systemic glycaemia", Nature Communications 9, 367, 13 pages (2018).
Lonn, M, et al., "Adipocyte size predicts incidence of type 2 diabetes in women", FASEB J 24(1), 326-231 (2010).
Manning, B, et al., "AKT/PKB Signaling: Navigating the Network", Cell 169, 381-405 (2017).
Must, A, et al., "The disease burden associated with overweight and obesity", JAMA 282(16), 1523-1529 (1999).
Patent Cooperation Treaty, International Searching Authority, Search Report and Written Opinion for PCT/US2017/045582, 9 pages, Oct. 13, 2017.
Qiu, Z, et al., "SWELL1, a plasma membrane protein, is an essential component of volume-regulated anion channel", Cell 157(2), 447-458 (2014).
Salans, L, et al., "The role of adipose cell size and adipose tissue insulin sensitivity in the carbohydrate intolerance of human obesity", J Clin Invest 47(1), 153-165 (1968).

(Continued)

*Primary Examiner* — Irina Neagu
(74) *Attorney, Agent, or Firm* — Viksnins Harris Padys Malen LLP

(57) ABSTRACT

The invention provides the use of SWELL1 inhibitors and modulators for therapeutic use, e.g., to treat obesity and type 2 diabetes.

7 Claims, 1 Drawing Sheet

(56) References Cited

OTHER PUBLICATIONS

Shoham, N., et al., "Static mechanical stretching accelerates lipid production in 3T3-L1 adipocytes by activating the MEK signaling pathway", Am J Physiol Cell Physiol 302(2), C429-C441 (2012).
Shojam, N., et al., "Adipocyte Stiffness Increases with Accumulation of Lipid Droplets", Biophys J 106(6), 1421-1431 (2014).
Voss, F, et al., "Identification of LRRC8 heteromers as an essential component of the volume-regulated anion channel VRAC", Science 344(6184), 634-638 (2014).
Weyer, C, et al., "Enlarged subcutaneous abdominal adipocyte size, but not obesity itself, predicts type II diabetes independent of insulin resistance", Diabetologia 43(12), 1498-1506 (2000).
Xie, L, et al., "Induction of adipose and hepatic SWELL1 expression is required for maintaining systemic insulin-sensitivity in obesity", Channels 11(6), 673-677 (2017).
Zhang, Y, et al., "SWELL1 is a regulator of adipocyte size, insulin signalling and glucose homeostasis", Nat Cell Biol 19(5), 504-517 (2017).
Kang, et al., "SWELL1 is a glucose sensor required for (3-cell excitability and insulin secretion", bioRxiv preprint, 2017; doi: http://dx.doi.Org/10.1101/155093.
Alghanem, A, et al., "The SWELL1-LRRC8 complex regulates endothelial AKT-eNOS signaling and vascular function", eLife 10 (e61313), 1-29 (2021).
Gunasekar, S, et al., "Small molecule SWELL1 complex induction improves glycemic control and nonalcoholic fatty liver disease in murine Type 2 diabetes", Nature Communications 13(784), 1-25 (2022).
Gunasekar, S, et al., "SWELL signalling in adipocytes: can fat 'feel' fat?", Adipocyte 8(1), 223-228 (2019).
Kumar, A, et al., "SWELL1 regulates skeletal muscle cell size, intracellular signaling, adiposity and glucose metabolism", Elife 9 (e58941), 1-27 (2020).
Menegaz, D, et al., "Mechanism and effects of pulsatile GABA secretion from cytosolic pools in the human beta cell", Nat Metab 1(11), 1110-1126 (2019).
Zhou, J, et al., "LRRC8A-dependent volume-regulated anion channels contribute to ischemia-induced brain injury and glutamatergic input to hippocampal neurons", Exp Neurol 332 (113391), 1-23 (2020).
Hamood, R, et al., "Diabetes After Hormone Therapy in Breast Cancer Survivors: A Case-Cohort Study", Journal of Clinical Oncology 36, 2061-2069 (2018).
Lipscombe, L, et al., "Association Between Tamoxifen Treatment and Diabetes", Cancer 118, 2615-2622 (2012).
Best et al., "Electrical activity in pancreatic islet cells: The VRAC hypothesis", Islets, 2:2, 59-64, (2010) DOI: 10.4161/sl.2.2.11171.

* cited by examiner

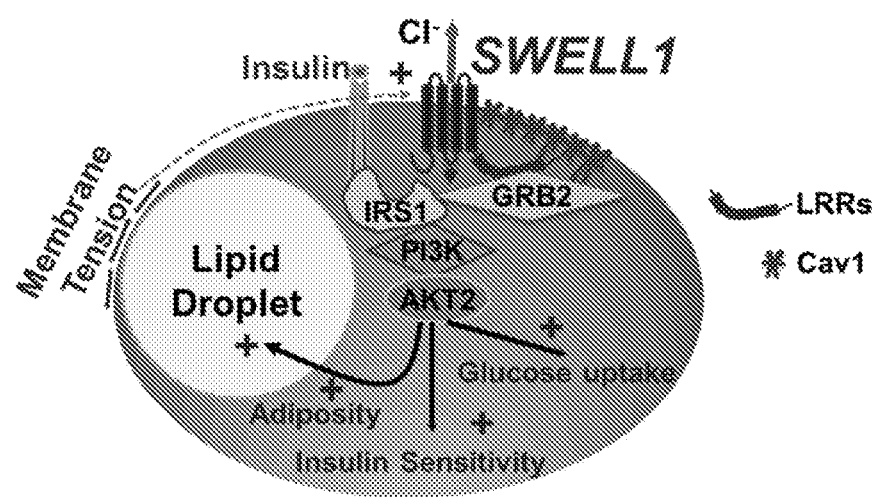

USE OF SWELL1 INHIBITORS AND MODULATORS TO TREAT TYPE 2 DIABETES AND OBESITY

RELATED APPLICATIONS

This application claims the benefit of priority of U.S. Provisional Application Ser. No. 62/371,061 filed on Aug. 4, 2016, and U.S. Provisional Application Ser. No. 62/489,265 filed on Apr. 24, 2017, which applications are herein incorporated by reference.

STATEMENT OF GOVERNMENT SUPPORT

This invention was made with government support under NIDDK 1R01DK106009 awarded by the National Institutes of Health. The government has certain rights in the invention.

BACKGROUND

Obesity is a disease that, in addition to being a major public health problem in the United States and world-wide, causes a predisposition to developing Type 2 diabetes. Currently, obesity treatments are fairly ineffective and have side effects, which are often severe. As such, understanding the biology connecting obesity with Type 2 diabetes and developing new therapeutic approaches to treat obesity and Type 2 diabetes will have a significant impact on the health of the world population and are needed.

SUMMARY OF CERTAIN EMBODIMENTS OF THE INVENTION

Obesity is a major world-wide public health problem, predisposing patients to diabetes, heart disease, and cancer, and inflicting healthcare costs over 100 billion dollars in the U.S. alone. Adipocytes have a remarkable ability to enlarge, increasing in volume by more than 30 times in the setting of obesity. Glucose intolerance and type 2 diabetes in obesity are most strongly associated with increases in adipocyte size, suggesting adipocyte-autonomous stretch-sensitive mechanisms may regulate insulin sensitivity. To examine this, the patch-clamp technique was applied to mature adipocytes and a novel stretch/swell-activated ionic current characteristic of the Volume-Regulated Anion Current encoded by LRRC8a (SWELL1) was discovered. Using shRNA and CRISPR/cas9-mediated SWELL1 silencing, it was discovered that SWELL1 encodes this stretch/swell current in primary and cultured adipocytes. SWELL1 loss of function disrupts insulin-PI3K-AKT2 signaling in adipocytes in vitro and in vivo. Consistent with this effect of SWELL1 on insulin signaling, SWELL1 knock-down in obese mice exacerbates insulin resistance. Remarkably, application of the selective SWELL1 inhibitor DCPIB to cultured adipocytes induced a compensatory increase in SWELL1 protein expression. When administered to mice raised on a high-fat diet, DCPIB normalized glucose tolerance associated with obesity. These findings provide an in vivo proof of concept that DCPIB (and other SWELL1 inhibitors, e.g., small molecule SWELL1 inhibitors) can induce a compensatory increase in SWELL1 expression, which can positively modulate insulin sensitivity in the context of Type 2 diabetes.

Accordingly, certain embodiments of the present invention provide a method of treating adipocyte expansion, protecting against ischemic damage in myocardial infarction, ischemic stroke, and cancer, treating diabetes (e.g., type 2 diabetes) and obesity, using a SWELL1 inhibitor, such as DCPIB, clomiphene, nafoxidine or tamoxifen.

BRIEF DESCRIPTION OF THE FIGURE

FIG. 1 provides a schematic description of certain aspects of the SWELL1 pathway, which illustrates SWELL1 as a sensor of adipocyte volume and a positive regulator of adipocyte growth and insulin signaling. (see also, Manning and Toker, Cell, 169, 381 (2017)).

DETAILED DESCRIPTION

Certain embodiments of the present invention provide a method for treating obesity in a patient in need of such treatment, comprising administering to the patient a therapeutically effective amount of a SWELL1 inhibitor to the patient.

Certain embodiments of the present invention provide a method for treating diabetes (e.g., type 2 diabetes) in a patient in need of such treatment, comprising administering to the patient a therapeutically effective amount of a SWELL1 inhibitor to the patient.

Certain embodiments of the present invention provide a method for increasing insulin sensitivity in a patient in need of such treatment, comprising administering to the patient a therapeutically effective amount of a SWELL1 inhibitor to the patient.

Certain embodiments of the present invention provide a SWELL1 inhibitor for treating obesity.

Certain embodiments of the present invention provide the use of a SWELL1 inhibitor for treating diabetes, e.g., type 2 diabetes.

Certain embodiments of the present invention provide the use of a SWELL1 inhibitor for increasing insulin sensitivity.

Certain embodiments of the present invention provide the use of a SWELL1 inhibitor as a weight loss treatment.

In certain embodiments, the SWELL1 inhibitor is DCPIB, clomiphene, nafoxidine or tamoxifen.

In certain embodiments, the SWELL1 inhibitor is DCPIB.

In certain embodiments, the administration or use of the SWELL1 inhibitor is sufficient to upregulate the expression of SWELL1.

Certain embodiments of the present invention provide a method for treating obesity in a patient in need of such treatment, comprising administering to the patient a therapeutically effective amount of a SWELL1 inhibitor or modulator to the patient.

Certain embodiments of the present invention provide a method for treating diabetes (e.g., type 2 diabetes) in a patient in need of such treatment, comprising administering to the patient a therapeutically effective amount of a SWELL1 inhibitor or modulator to the patient.

Certain embodiments of the present invention provide a method for increasing insulin sensitivity in a patient in need of such treatment, comprising administering to the patient a therapeutically effective amount of a SWELL1 inhibitor or modulator to the patient.

Certain embodiments of the present invention provide a SWELL1 inhibitor or modulator for treating obesity.

Certain embodiments of the present invention provide the use of a SWELL1 inhibitor or modulator for treating diabetes, e.g., type 2 diabetes.

Certain embodiments of the present invention provide the use of a SWELL1 inhibitor or modulator for increasing insulin sensitivity.

Certain embodiments of the present invention provide the use of a SWELL1 inhibitor or modulator as a weight loss treatment.

In certain embodiments, the SWELL1 inhibitor or modulator is DCPIB, clomiphene, nafoxidine or tamoxifen or a compound that modulates SWELL1 activity or expression levels. In certain embodiments, the compound is a compound of formula I, II, III or IV, or a salt thereof.

In certain embodiments, the SWELL1 inhibitor or modulator is DCPIB.

In certain embodiments, the administration or use of the SWELL1 inhibitor or modulator is sufficient to upregulate the expression of SWELL1, and/or accessory proteins, including but not limited to LRRC8b, LRRC8c, LRRC8d, LRRC8e, GRB2, Cav1, IRS1, IRS2.

Certain embodiments of the present invention provide a method for treating obesity in a patient in need of such treatment, comprising administering to the patient a therapeutically effective amount of a SWELL1 inhibitor or modulator to the patient, or a modulator of associated SWELL1 proteins, including LRRC8b, c, d or e. In certain embodiments, a modulator may alter the channel activity of SWELL1 channel complexes or the signaling role via leucine-rich repeat domains or other protein association domains.

Certain embodiments of the present invention provide a method for treating diabetes (e.g., type 2 diabetes) in a patient in need of such treatment, comprising administering to the patient a therapeutically effective amount of a SWELL1 inhibitor or modulator to the patient, or a modulator of associated SWELL1 proteins, including LRRC8b, c, d or e. In certain embodiments, a modulator may alter the channel activity of SWELL1 channel complexes or the signaling role via leucine-rich repeat domains or other protein association domains.

Certain embodiments of the present invention provide a method for increasing insulin sensitivity in a patient in need of such treatment, comprising administering to the patient a therapeutically effective amount of a SWELL1 inhibitor or modulator to the patient, or a modulator of associated SWELL1 proteins, including LRRC8b, c, d or e. In certain embodiments, modulator may alter the channel activity of SWELL1 channel complexes or the signaling role via leucine-rich repeat domains or other protein association domains.

Certain embodiments of the present invention provide the use of a SWELL1 inhibitor or modulator for treating obesity.

Certain embodiments of the present invention provide the use of a SWELL1 inhibitor or modulator for treating diabetes, e.g., type 2 diabetes.

Certain embodiments of the present invention provide the use of a SWELL1 inhibitor or modulator for increasing insulin sensitivity.

Certain embodiments of the present invention provide the use of a SWELL1 inhibitor or modulator as a weight loss treatment.

In certain embodiments, the SWELL1 inhibitor or modulator is DCPIB, clomiphene, nafoxidine or tamoxifen.

In certain embodiments, the SWELL1 inhibitor or modulator is a compound of formula I, II, III, or IV, or a salt thereof.

In certain embodiments, the SWELL1 inhibitor or modulator is DCPIB.

In certain embodiments, the modulator alters pannexin channel activity, expression or function, as pannexin proteins are homologous to SWELL1/LRRC8 proteins.

In certain embodiments, the administration or use of the SWELL1 inhibitor or modulator is sufficient to upregulate the expression of SWELL1, or alter expression of SWELL1 associated proteins including LRRC8b,c,d,e, GRB2, Cav1, IRS1, IRS2.

Certain embodiments of the present invention provide use of a SWELL1 inhibitor or modulator for increasing insulin secretion.

Certain embodiments of the present invention provide a method for increasing insulin secretion in a patient in need of such treatment, comprising administering to the patient a therapeutically effective amount of a SWELL1 inhibitor or modulator to the patient.

In certain embodiments, the methods or uses treat diabetic retinopathy and/or diabetic neuropathy.

In certain embodiments, the methods or uses for treating diabetes reduce the development of diabetes among individuals meeting the clinical criteria for pre-diabetes.

The discoveries presented herein also can be used, in certain embodiments, as a basis to screen for compounds that would be useful for treating obesity, for treating diabetes, e.g., type 2 diabetes, for increasing insulin sensitivity, for increasing insulin secretion or identifying compounds for use as a weight loss treatment, comprising determining whether the compound is a SWELL1 inhibitor or modulator.

Further, it is herein described that SWELL1 coordinately regulates both insulin secretion and insulin sensitivity in response to a nutrient load, highlighting SWELL1 as a virtual nutrient sensor and rheostat of systemic glucose metabolism.

It is further described that pharmacological strategies that augment SWELL1 activity/signaling in adipocytes (or in other insulin-sensitive peripheral tissues expressing SWELL1) are expected to enhance insulin signaling and improve systemic glycaemia in the setting of obesity-induced diabetes.

Obesity results largely from massive volumetric expansion of constituent adipocytes. It is this increase in adipocyte size that is tightly associated with metabolic disease, implicating the action of an undiscovered volume-sensing signaling molecule in adipocytes. Here, adipocyte patch-clamp is combined with shRNA- and CRISPR/cas9-mediated gene silencing to show that SWELL1 (LRRC8a), a member of the Leucine Rich Repeat Containing protein family, encodes a volume-sensitive current in adipocytes. SWELL1 is induced and activated in hypertrophic adipocytes in the setting of obesity and is required for adipocyte hypertrophy and glucose uptake. Moreover, SWELL1 modulates adipocyte insulin signaling via C-terminal leucine-rich repeat domain interactions with GRB2/Cav1 and PI3K-AKT pathway. In vivo, SWELL1 knock-down reduces adipocyte size, fat mass and exacerbates glucose intolerance in obese mice. These studies identify SWELL1 as a cell-autonomous sensor of adipocyte size that regulates adipocyte growth, insulin sensitivity and glucose tolerance in the setting of obesity.

Further, insulin secretion from the pancreatic β-cell is initiated by calcium influx through voltage-gated $Ca^{2+}$ channels (VGCC) to trigger insulin vesicle fusion with the β-cell plasma membrane. The firing of VGCC depends on the β-cell membrane potential, which is in turn mediated by the balance of depolarizing (excitatory) and hyperpolarizing (inhibitory) ionic currents. While much attention has focused on inhibitory hyperpolarizing potassium currents, there is little knowledge about the requisite excitatory currents required to depolarize the β-cell, including the molecular identity of these excitatory currents. One candidate for a depolarizing current is a chloride conductance known as the volume-regulatory anion current (VRAC) or $I_{Cl,SWELL}$. Here it is shown, using shRNA and CRISPR/cas9 gene silencing combined with β-cell patch-clamp, that SWELL1 (LRRC8a) mediates $I_{Cl,SWELL}$ in β-cells. SWELL1-mediated $I_{Cl,SWELL}$ activates in response to hypotonic and glucose-stimulated β-cell swelling. SWELL1-depletion entirely disrupts both glucose-stimulated and hypotonic swell-mediated activation of VGCC-dependent intracellular calcium signaling in β-cells. Finally, SWELL1 KO MIN6 cells and β-cell targeted SWELL1 KO murine islets exhibit significantly impaired glucose-stimulated insulin secretion, with preserved insulin content. These results reveal a physiological role for SWELL1 as a glucose sensor—linking glucose-mediated β-cell swelling to SWELL1-dependent activation of VGCC-triggered calcium signaling and insulin secretion. These findings highlight the importance of SWELL1 in swell-mediated β-cell activation, a form of "swell-secretion" coupling important for glucose-stimulated insulin secretion.
Adipocytes The adipocyte has been optimized over several hundred million years to maximize energy storage by forming a large lipid droplet, separated from the plasma membrane by only a thin rim (~300 nm) of cytoplasm, with nucleus and other organelles pushed aside. The adipocyte is also unique in its tremendous capacity for volumetric expansion, increasing by more than 30-fold in the setting of obesity to accommodate the expanding lipid droplet during times of plenty (Farnier et al., *Int J Obes Relat Metab Disord,* 27, 1178-1186 (2003)). These findings lead to some interesting questions: Could the growing lipid droplet mechanically interact with the plasma membrane to increase membrane tension? Could there be molecular "stretch" sensors active within the adipocyte plasma membrane that may signal to lipid growth pathways? There are several recent studies in the bioengineering field that link adipocyte lipid droplet expansion with increases in adipocyte stiffness and reduced membrane compliance (Shoham et al., *Biophys J,* 106, 1421-1431 (2014)), in addition to a relationship between membrane tension and activation of adipogenic MAP Kinase signaling pathways (Shoham et al., *Am J Physiol Cell Physiol,* 302, C429-441 (2012); Pellegrinelli et al., *The Journal of pathology,* 233, 183-195 (2014)). Moreover, adipocyte size correlates in obesity (as opposed to number) and the severity of linked diseases such as diabetes and insulin resistance (Salans et al., *J Clin Invest,* 47, 153-165 (1968); Weyer et al., *Diabetologia,* 43, 1498-1506 (2000); Khan et al., *Molecular and cellular biology,* 29, 1575-1591 (2009)). Other studies propose that caveolae allow expanding adipocytes to autoregulate lipid content based on mechanical lipid droplet-plasma membrane interactions and tune insulin signaling in response to adipocyte swelling (Briand et al., *Diabetes,* 63, 4032-4044 (2014); Eduardsen et al., *Cell Physiol Biochem,* 28, 1231-1246 (2011)).

Ion channels are membrane proteins that can signal in response to membrane-stretch. There are a number of candidate stretch/mechano-sensitive ion channels in mammalian cells including TRPM7, TRPV2, TRPV4, TRPC6 and Piezo-1/Piezo-2. Many of these ion channels are expressed in adipocytes, and have signaling roles important for adipogenesis, fatty acid sensing, oxidative metabolism, inflammation and energy homeostasis (Che et al., *Pflugers Arch,* 466, 947-959 (2014); Sukumar et al., *Circ Res,* 111, 191-200 (2012); Ye et al., *Cell,* 151, 96-110 (2012)).

As described herein, the swell-activated ion channel signaling in adipocytes was explored by applying the patch-clamp technique to freshly isolated, mature murine and human adipocytes that were mechanically swelled by applying positive pressure intracellularly or by osmotic swelling with hypotonic solution. Using this approach, a prominent swell-activated chloride current (SAC) was discovered in adipocytes encoded by the gene LRRC8a, a member of the Leucine Rich Repeat (LRR) Containing proteins (Voss et al., *Science,* 344, 634-638 (2014); Qiu et al., *Cell,* 157, 447-458 (2014)); renamed SWELL1 by Qiu and colleagues. As described herein, it was hypothesized that SWELL1 may sense adipocyte volume during physiological or pathophysiological adipocyte expansion and engage insulin-PI3K-AKT signaling, thereby coupling adipocyte size with growth and insulin sensitivity. Herein, the volume-sensitive SWELL1 molecule is linked to adipocyte insulin signaling, growth and systemic glucose homeostasis. Accordingly, a model is proposed in which SWELL1 tracks adipocyte expansion, and accordingly tunes insulin-mediated activation of growth and glucose import pathways. This discovery allows for the development of improved methods for treating type 2 diabetes and obesity.

The data presented herein show that the swell-activated molecule, SWELL1 is highly expressed in adipocytes, is enriched and activated in the context of adipocyte hypertrophy in obesity, and is required for maintaining adipocyte size, insulin sensitivity and glucose homeostasis via a LRRD-mediated GRB2 interaction with the insulin-PI3K-AKT2 signaling pathway. These findings link the volume-sensitive molecule, SWELL1, with adipocyte insulin-PI3K signaling and provide a molecular mechanism for the effects of adipocyte membrane tension on lipogenesis and intracellular signaling. Based on the data presented herein, a working model is presented in which SWELL1 is activated by increases in adipocyte volume during adipocyte hypertrophy, and this potentiates insulin-PI3K-AKT2 signaling via C-terminal LRRD interactions with GRB2-Cav1-IRS1-IR to support insulin-mediated glucose import and lipogenesis. In this model, SWELL1 senses adipocyte volumetric expansion and acts as a feed-forward amplifier to further promote adipocyte expansion, energy storage, and enhance insulin sensitivity during times of caloric excess (feeding).

While it is tempting to connect SWELL1-mediated channel activity with its signaling role either via SWELL1 conformational changes or ion permeation, and while not intending to be limited by this hypothesis, an alternative possibility is that SWELL1 Leucine-Rich Repeat Domains (LRRD) provide docking surfaces for protein-protein interactions and passively promote the association of components of the insulin signaling cascade (GRB2), or other signaling pathways. In this case there may be no direct relationship between SWELL1-mediated channel activation and insulin-PI3K-AKT signaling. Further, SWELL1 forms heteromultimers with LRRC8b-e, which modifies channel gating, and may also influence the diversity of molecular interactions with different protein partners based on the relative abundance of LRRC8b-e. Therefore it is possible that, depending in the expression profile of LRRC8 proteins in different tissues, SWELL1 modulation of intracellular signaling may vary in a cell-type dependent fashion.

An intriguing observation is that SWELL1 deficiency specifically prevents insulin-PI3K-AKT2 signaling and glucose uptake despite a constitutive increase in AKT1 signaling. Indeed, both cellular and in vivo phenotypes are entirely consistent with previous AKT2-selective loss of function studies, including insulin resistance, reduced adiposity and glucose intolerance. Conversely, AKT1 is dispensable for maintenance of glucose homeostasis but is instead required for organismal growth and development. Moreover, recent work highlights AKT2 over AKT1 as required for adipogenesis in the setting of obesity. Thus, targeting the SWELL1-PI3K-AKT2 axis may represent a novel approach to specifically modulate AKT2 effects on adiposity and insulin sensitivity without altering adipose tissue development. Further molecular studies to determine the mechanism for biased SWELL1-PI3K-AKT2 over AKT1 signaling are also warranted.

The LRRD-mediated SWELL1-GRB2-Cav1 molecular interaction connecting SWELL1 to insulin-PI3K-AKT2 signaling is both consistent with the SWELL1(LRRC8a)-GRB2-GAB2-LCK complex reported in lymphocytes and also provides a molecular mechanism for the observed defect in insulin-PI3K-AKT2 signaling upon adipocyte SWELL1 ablation. Likewise, the SWELL1-Cav1 interaction is also compelling as this positions SWELL1 within caveolae, which are abundant in adipocytes, are thought to form insulin-signaling microdomains and are required for normal insulin and PI3K-AKT signaling. Indeed, Cav1 KO mice on a HFD are phenotypically similar to AAV/Rec2-mediated SWELL1 KD mice with respect to adiposity and insulin-sensitivity.

Insulin-stimulation reduces both SWELL1-GRB2 and Cav1-GRB2, but not SWELL1-Cav1 interactions in WT 3T3-F442A adipocytes. This suggests that insulin-stimulation induces GRB2 dissociation from the insulin-signaling complex. Curiously, this insulin-mediated GRB2 dissociation from Cav1 is abrogated upon SWELL1 ablation, implying that SWELL1 may tune insulin signaling by titrating GRB2-interactions with components of the insulin signaling complex. This intriguing hypothesis warrants further investigation.

In summary, as described herein, it has been discovered that the volume-sensitive membrane protein SWELL1 can respond to increases in adipocyte size and is a positive regulator of adipocyte lipid content and glucose uptake though modulation of insulin-PI3K-AKT2 signaling via GRB2-mediated interactions, particularly in the setting of obesity, and thus provides a pharmacological target for treating diseases such as type 2 diabetes and obesity.

SWELL1 Inhibitors and Modulators

Embodiments of the present invention are directed to the use of SWELL1 inhibitors and modulators to treat diseases such as type 2 diabetes and obesity.

DCPIB

DCPIB (4-[(2-Butyl-6,7-dichloro-2-cyclopentyl-2,3-dihydro-1-oxo-1H-inden-5-yl)oxy]butanoic acid), a selective SWELL1 inhibitor, is a potent and selective inhibitor of the volume-sensitive anion channel (VSAC) in rat pancreatic β-cells and $I_{Cl, swell}$ in various cardiovascular tissues. DCPIB is an example of a SWELL1 inhibitor useful in the practice of certain embodiments of the invention.

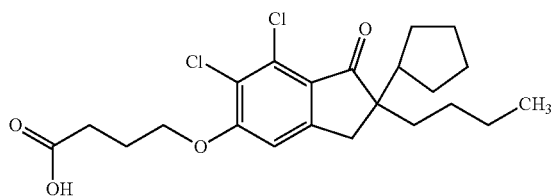 [SMILES: CCCCC1(C2CCCC2)Cc2cc(OCCCC(=O)O)c(Cl)c(Cl)c2C1=O]

Other SWELL1 inhibitors and modulators include clomiphene, nafoxidine and tamoxifen and compounds as described below, or salts thereof.

Accordingly, in certain embodiments the SWELL1 inhibitor or modulator is a compound of formula I

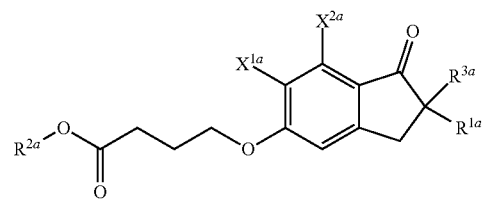

wherein:
$X^{1a}$ and $X^{2a}$ are independently halo;
$R^{1a}$ is $C_{1-6}$ alkyl, 3-6 membered cycloalkyl, or phenyl, wherein the $C_{1-6}$ alkyl is optionally substituted with 3-6 membered cycloalkyl;
$R^{2a}$ is hydrogen or $C_{1-6}$ alkyl, wherein the $C_{1-6}$ alkyl is optionally substituted with carboxy; and
$R^{3a}$ is $C_{1-6}$ alkyl;
or a pharmaceutically acceptable salts thereof.

In certain embodiments, the compound is a compound of the following formula, or a salt thereof (see: U.S. Pat. No. 4,465,850)

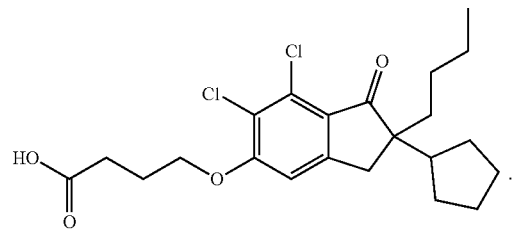 [SMILES: CCCCC1(C2CCCC2)Cc2cc(OCCCC(=O)O)c(Cl)c(Cl)c2C1=O]

In certain embodiments the SWELL1 inhibitor or modulator is a compound of formula II

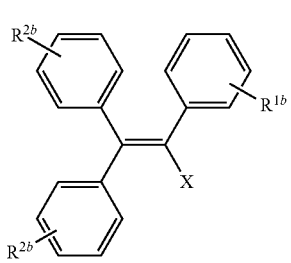

wherein:
$R^{1b}$ is hydrogen, halo or methoxy;
only one of $R^{2b}$ is —O(CH$_2$)$_n$—NR$^{3b}$R$^{4b}$;
the other $R^{2b}$ is hydrogen, halo or methoxy;
each of $R^{3b}$ and $R^{4b}$ is independently H or $C_{1-6}$ alkyl, or $R^{3b}$ and $R^{4b}$ together with the nitrogen to which they are attached form aziridino, azetidino, morpholino, piperazino, pyrrolidino or piperidino;
n is an integer from 2 to 4; and
X is halo;
or a pharmaceutically acceptable salt thereof.

In certain embodiments, the compound is a compound of the following formula, or a salt thereof. (see U.S. Pat. No. 2,914,563)

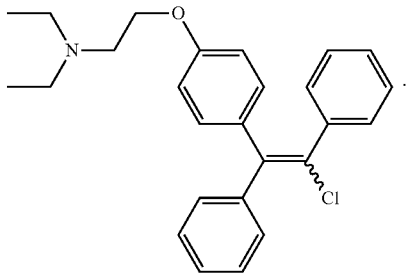 [SMILES: CCN(CC)CCOc1ccc(C(=C(Cl)c2ccccc2)c2ccccc2)cc1]

In certain embodiments the SWELL1 inhibitor or modulator is a compound of formula III

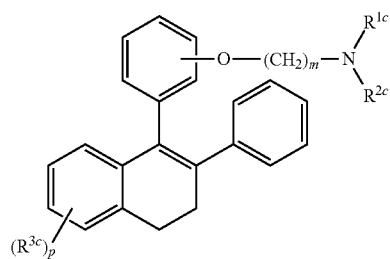

wherein:
each of $R^{1c}$ and $R^{2c}$ is independently H or $C_{1-8}$ alkyl, or $R^{1c}$ and $R^{2c}$ together with the nitrogen to which they are attached form aziridino, azetidino, morpholino, piperazino, pyrrolidino or piperidino; wherein the aziridino, azetidino, morpholino, piperazino, pyrrolidino and piperidino are optionally substituted with one or more $C_{1-6}$ alkyl;

m is an integer from 2 to 6, $R^{3c}$ is $C_{1-8}$ alkoxy; and p is an integer from 1 to 4;

or a pharmaceutically acceptable salt thereof.

In certain embodiments, the compound is a compound of the following formula, or a salt thereof. (see U.S. Pat. No. 3,274,213)

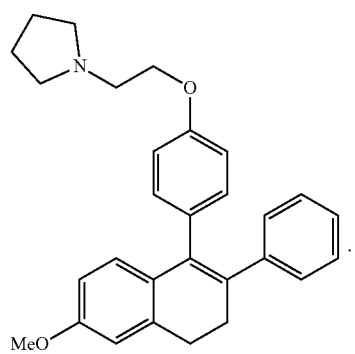 [SMILES: COc1ccc2c(c1)CCC(c1ccccc1)=C2c1ccc(OCCN2CCCC2)cc1]

In certain embodiments the SWELL1 inhibitor or modulator is a compound of formula IV

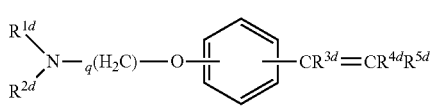

wherein:
each of $R^{1d}$ and $R^{2d}$ is independently H or $C_{1-6}$ alkyl, or $R^{1d}$ and $R^{2d}$ together with the nitrogen to which they are attached form aziridino, azetidino, morpholino, piperazino, pyrrolidino or piperidino;

each of $R^{3d}$ and $R^{4d}$ is independently aryl which is optional substituted with one or more groups selected from $C_{1-6}$ alkyl, $C_{1-6}$ alkoxy, $C_{1-6}$ dialkylamino, or halo;

$R^{5d}$ is $C_{1-6}$ alkyl or $C_{1-6}$ alkenyl, wherein the $C_{1-6}$ alkyl is optionally substituted with aryl; and q is an integer from 2 to 6;

or a pharmaceutically acceptable salt thereof.

In certain embodiments, the compound is a compound of the following formula, or a salt thereof. (see U.S. Pat. No. 4,536,516)

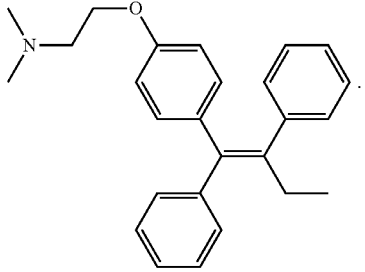 [SMILES: CC/C(=C(\c1ccccc1)c1ccc(OCCN(C)C)cc1)c1ccccc1]

"Systemic delivery," as used herein, refers to delivery of agents that lead to a broad biodistribution of an active agent within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a desired site distal to the site of administration. Systemic delivery of active agents (e.g., SWELL1 inhibitors and modulators) can be by any means known in the art including, for example, intravenous, subcutaneous, and intraperitoneal. In a preferred embodiment, systemic delivery is by intravenous delivery.

"Local delivery," as used herein, refers to delivery of an active agent such as a siRNA directly to a target site within an organism. For example, an agent can be locally delivered by direct injection into a disease site, other target site, or a target organ such as the liver, heart, pancreas, kidney, and the like.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

An "effective amount" of an agent, e.g., a pharmaceutical formulation, refers to an amount effective, at dosages and for periods of time necessary, to achieve the desired therapeutic or prophylactic result. In some embodiments, the effective amount refers to an amount of a SWELL1 inhibitor or modulator that (i) treats the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein.

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include one or more of preventing occurrence or recurrence of disease, alleviation of symptoms, diminishment of any direct or indirect pathological consequences of the disease, stabilized (i.e., not worsening) state of disease, decreasing the rate of disease progression, amelioration or palliation of the disease state, prolonging survival as compared to expected survival if not receiving treatment and remission or improved prognosis. In certain embodiments, a SWELL1 inhibitor or modulator is used to delay development of a disease or disorder or to slow the progression of a disease or disorder. Those individuals in need of treatment include those already with the condition or disorder as well as those prone to have the condition or disorder, (for example, through a genetic mutation or aberrant expression of a gene or protein) or those in which the condition or disorder is to be prevented.

As used herein, "delaying progression of a disease" means to defer, hinder, slow, retard, stabilize, and/or postpone development of the disease (such as type 2 diabetes and/or obesity). This delay can be of varying lengths of time, depending on the history of the disease and/or individual being treated. As is evident to one skilled in the art, a sufficient or significant delay can, in effect, encompass prevention, in that the individual does not develop the disease.

Further provided herein are pharmaceutical compositions that comprise a SWELL1 inhibitor or modulator for use in the methods described herein, e.g., to treat type 2 diabetes or obesity. In one embodiment, the composition further comprises a pharmaceutically acceptable carrier, adjuvant, or vehicle. In another embodiment, the composition further comprises an amount of the compound effective to measurably inhibit SWELL1, modulate SWELL1 activity or increase SWELL1 expression level, or associated protein partners. In certain embodiments, the composition is formulated for administration to a patient in need thereof.

Compositions comprising a SWELL1 inhibitor or modulator or salt thereof may be administered orally, parenterally, by inhalation spray, topically, transdermally, rectally, nasally, buccally, sublingually, vaginally, intraperitoneal, intrapulmonary, intradermal, epidural or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

In one embodiment, the composition comprising a SWELL1 inhibitor or modulator or salt thereof is formulated as a solid dosage form for oral administration. Solid dosage forms for oral administration include capsules, tablets, pills, powders, and granules. In certain embodiments, the solid oral dosage form comprising a SWELL1 inhibitor or modulator or a salt thereof further comprises one or more of (i) an inert, pharmaceutically acceptable excipient or carrier, such as sodium citrate or dicalcium phosphate, and (ii) filler or extender such as starches, lactose, sucrose, glucose, mannitol, or silicic acid, (iii) binders such as carboxymethylcellulose, alginates, gelatin, polyvinylpyrrolidinone, sucrose or acacia, (iv) humectants such as glycerol, (v) disintegrating agent such as agar, calcium carbonate, potato or tapioca starch, alginic acid, certain silicates or sodium carbonate, (vi) solution retarding agents such as paraffin, (vii) absorption accelerators such as quaternary ammonium salts, (viii) a wetting agent such as cetyl alcohol or glycerol monostearate, (ix) absorbent such as kaolin or bentonite clay, and (x) lubricant such as talc, calcium stearate, magnesium stearate, polyethylene glycols or sodium lauryl sulfate. In certain embodiments, the solid oral dosage form is formulated as capsules, tablets or pills. In certain embodiments, the solid oral dosage form further comprises buffering agents. In certain embodiments, such compositions for solid oral dosage forms may be formulated as fillers in soft and hard-filled gelatin capsules comprising one or more excipients such as lactose or milk sugar, polyethylene glycols and the like.

In certain embodiments, tablets, dragees, capsules, pills and granules of the compositions comprising a SWELL1 inhibitor or modulator or salt thereof optionally comprise coatings or shells such as enteric coatings. They may optionally comprise opacifying agents and can also be of a composition that they release the active ingredient(s) only, or preferentially, in a certain part of the intestinal tract, optionally, in a delayed manner. Examples of embedding compositions include polymeric substances and waxes, which may also be employed as fillers in soft and hard-filled gelatin capsules using such excipients as lactose or milk sugar as well as high molecular weight polethylene glycols and the like.

In another embodiment, a composition comprises a micro-encapsulated SWELL1 inhibitor or modulator or salt thereof, and optionally, further comprises one or more excipients.

In another embodiment, compositions comprise liquid dosage formulations comprising a SWELL1 inhibitor or modulator or salt thereof for oral administration, and optionally further comprise one or more of pharmaceutically acceptable emulsions, microemulsions, solutions, suspensions, syrups and elixirs. In certain embodiments, the liquid dosage form optionally, further comprise one or more of an inert diluent such as water or other solvent, a solubilizing agent, and an emulsifier such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols or fatty acid esters of sorbitan, and mixtures thereof. In certain embodiments, liquid oral compositions optionally further comprise one or more adjuvant, such as a wetting agent, a suspending agent, a sweetening agent, a flavoring agent and a perfuming agent.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a SWELL1 inhibitor or modulator, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In certain embodiments, the composition for rectal or vaginal administration are formulated as suppositories which can be prepared by mixing a SWELL1 inhibitor or modulator or a salt thereof with suitable non-irritating excipients or carriers such as cocoa butter, polyethylene glycol or a suppository wax, for example those which are solid at ambient temperature but liquid at body temperature and therefore melt in the rectum or vaginal cavity and release the SWELL1 inhibitor or modulator.

Example dosage forms for topical or transdermal administration of a SWELL1 inhibitor or modulator include ointments, pastes, creams, lotions, gels, powders, solutions, sprays, inhalants or patches. The SWELL1 inhibitor or modulator or a salt thereof is admixed under sterile conditions with a pharmaceutically acceptable carrier, and optionally preservatives or buffers. Additional formulation examples include an ophthalmic formulation, ear drops, eye drops, transdermal patches. Transdermal dosage forms can be made by dissolving or dispensing the SWELL1 inhibitor or modulator or a salt thereof in medium, for example ethanol or dimethylsulfoxide. Absorption enhancers can also be used to increase the flux of the compound across the skin. The rate can be controlled by either providing a rate controlling membrane or by dispersing the compound in a polymer matrix or gel.

Nasal aerosol or inhalation formulations of a SWELL1 inhibitor or modulator or a salt thereof may be prepared as solutions in saline, employing benzyl alcohol or other suitable preservatives, absorption promotors to enhance bioavailability, fluorocarbons, and/or other conventional solubilizing or dispersing agents.

In certain embodiments, pharmaceutical compositions may be administered with or without food. In certain embodiments, pharmaceutically acceptable compositions are administered without food. In certain embodiments, pharmaceutically acceptable compositions of this invention are administered with food.

Specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided SWELL1 inhibitor or modulator or salt thereof in the composition will also depend upon the particular compound in the composition.

In one embodiment, the effective amount of the compound administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 5 to about 100 mg of the compound of the invention.

An example tablet oral dosage form comprises about 2 mg, 5 mg, 25 mg, 50 mg, 100 mg, 250 mg or 500 mg of a SWELL1 inhibitor or modulator or salt thereof, and further comprises about 5-30 mg anhydrous lactose, about 5-40 mg sodium croscarmellose, about 5-30 mg polyvinylpyrrolidone (PVP) K30 and about 1-10 mg magnesium stearate. The process of formulating the tablet comprises mixing the powdered ingredients together and further mixing with a solution of the PVP. The resulting composition can be dried, granulated, mixed with the magnesium stearate and compressed to tablet form using conventional equipment. An example of an aerosol formulation can be prepared by dissolving about 2-500 mg of a compound of formula I or salt thereof, in a suitable buffer solution, e.g. a phosphate buffer, and adding a tonicifier, e.g. a salt such sodium chloride, if desired. The solution may be filtered, e.g. using a 0.2 micron filter, to remove impurities and contaminants.

The SWELL1 inhibitors or modulators or salts therof may be employed alone or in combination with other agents for treatment as described above. For example, the second agent of the pharmaceutical combination formulation or dosing regimen may have complementary activities to the SWELL1 inhibitor or modulator such that they do not adversely affect each other. The compounds may be administered together in a unitary pharmaceutical composition or separately.

The term "co-administering" refers to either simultaneous administration, or any manner of separate sequential administration, of a SWELL1 inhibitor or modulator or a salt thereof, and a further active pharmaceutical ingredient or ingredients. If the administration is not simultaneous, the compounds are administered in a close time proximity to each other. Furthermore, it does not matter if the compounds are administered in the same dosage form, e.g. one compound may be administered topically and another compound may be administered orally. Typically, any agent that has activity against a disease or condition being treated may be co-administered.

The term "patient" or "individual" as used herein, refers to an animal, such as a mammal, such as a human. In one embodiment, patient or individual refers to a human.

The term "mammal" refers to any mammalian species such as a human, mouse, rat, dog, cat, hamster, guinea pig, rabbit, livestock, and the like.

Recitation of ranges of values herein are merely intended to serve as a shorthand method of referring individually to each separate value falling within the range, unless otherwise indicated herein, and each separate value is incorporated into the specification as if it were individually recited herein.

As is understood by one skilled in the art, reference to "about" a value or parameter herein includes (and describes) embodiments that are directed to that value or parameter per se. For example, description referring to "about X" includes description of "X".

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. It is understood that aspect and embodiments of the invention described herein include "consisting" and/or "consisting essentially of" aspects and embodiments.

Certain embodiments of the invention will now be illustrated by the following non-limiting Examples.

Example 1

SWELL1 is a Regulator of Adipocyte Size, Insulin Signaling and Glucose Homeostasis Adipocytes undergo considerable volumetric expansion in the setting of obesity. It has been proposed that such marked increases in adipocyte size may be sensed via adipocyte-autonomous mechanisms to mediate size-dependent intracellular signaling. Here, it is shown that SWELL1 (LRRC8a), a member of the Leucine Rich Repeat Containing protein family, is an essential component of a volume-sensitive ion channel (VRAC) in adipocytes. SWELL1-mediated VRAC is augmented in hypertrophic murine and human adipocytes in the setting of obesity. SWELL1 regulates adipocyte insulin-PI3K-AKT2-GLUT4 signaling, glucose uptake and lipid content via SWELL1 C-terminal leucine-rich repeat domain interactions with GRB2/Cav1. Silencing GRB2 in SWELL1 KO adipocytes rescues insulin-pAKT2 signaling. In vivo, shRNA-mediated SWELL1 knock-down and adipose-targeted SWELL1 knock-out reduce adiposity and adipocyte size in obese mice while impairing systemic glycaemia and insulin-sensitivity. These studies identify SWELL1 as a cell-autonomous sensor of adipocyte size that regulates adipocyte growth, insulin sensitivity and glucose tolerance.

The adipocyte has been optimized to maximize energy storage by forming a large lipid droplet, separated from the plasma membrane by only a thin rim of cytoplasm. The adipocyte is also unique in its tremendous capacity for volumetric expansion, increasing by >30-fold in the setting of obesity during times of plenty. Studies have linked adipocyte lipid droplet expansion with increases in adipocyte stiffness and reduced membrane compliance, and have noted a relationship between adipocyte membrane tension and activation of signaling pathways, implying that adipocytes may be mechano-sensitive. Moreover, there is a long-standing literature that correlates adipocyte size in obesity (as opposed to number) and the severity of linked diseases such as diabetes and insulin resistance, suggesting that increases in adipocyte volume or membrane tension may contribute to adverse intracellular signaling. Others propose that caveolae enable expanding adipocytes to auto-regulate lipid content based on mechanical lipid droplet-plasma membrane interactions and tune insulin signaling in response to adipocyte swelling. However, the molecular identity a putative adipocyte volume sensor remains a mystery.

Ion channels are membrane proteins that can signal in response to membrane-stretch, and accordingly provide plausible candidates for adipocyte membrane stretch-sensors that bridge membrane tension with intracellular signaling. There are a number of candidate stretch/mechano-sensitive ion channels in mammalian cells including TRPM7, TRPV2, TRPV4, TRPC6 and Piezo-1/Piezo-2. Many of these ion channels are expressed in adipocytes, and have signaling roles important for adipogenesis, fatty acid sensing, oxidative metabolism, inflammation and energy homeostasis.

In this study, swell-activated ion channel signaling was explored in adipocytes by applying the patch-clamp technique to freshly isolated, mature murine and human adipocytes. Using this approach, a prominent swell-activated chloride current was identified in adipocytes, characteristic of the volume-regulated anion current (VRAC), and it was discovered that the gene LRRC8a, a member of the Leucine Rich Repeat (LRR) Containing proteins (SWELL1), is required for adipocyte VRAC. To the best of our knowledge, no studies have identified SWELL1 as a component of the adipocyte plasma membrane. It was hypothesized that SWELL1 may participate in sensing adipocyte volume during physiological or pathophysiological adipocyte expansion and engage insulin-PI3K-AKT signaling—thereby coupling adipocyte growth with insulin signaling. Herein, the volume-sensitive SWELL1 molecule is linked to adipocyte insulin signaling and growth; and proposed herein is a model in which SWELL1 activates in response to adipocyte expansion, and tunes insulin-mediated activation of growth and glucose import pathways.

Adipocyte Patch Clamp Reveals Prominent Swell-Activated Current in Murine and Human Adipocytes To identify a putative swell-activated ionic current in adipocytes, patch-clamp recordings were performed on mature murine adipocytes freshly isolated from inguinal white adipose tissue (iWAT). Ionic currents were measured in voltage-clamp mode while simultaneously swelling the adipocyte by applying positive pressure (~3-5 mmHg, whole-cell configuration) via the patch-pipette. After a few minutes, activation of a large swell-activated current was observed. This current is outward rectifying, characterized by larger outward current at positive voltages compared to inward currents at negative voltages during sequential voltage ramps or voltage steps, with the current amplitude proportional to the extent of adipocyte swelling. This current reverses direction at $-11.7\pm2.5$ mV, which is near the reversal potential of chloride under these conditions ($-11.5$ mV, junction potential corrected). Application of low chloride extracellular solution (5.4 mM CsCl) largely abolished the outward component of this current and shifted the current reversal towards 0 mV, suggesting a predominant chloride conductance. Finally, this swell-activated adipocyte current is blocked by 4-[(2-Butyl-6,7-dichloro-2-cyclopentyl-2,3-dihydro-1-oxo-1H-inden-5-yl)oxy]butanoic acid (DCPIB), a selective blocker of the volume-regulated anion current (VRAC) or volume-sensitive outwardly rectifying chloride current (VSOR). This swell-activated current was confirmed to be present in the murine 3T3-F442A and human adipocyte cell lines (NPAD) upon hypotonic swelling, and this current is fully inhibited by DCPIB. Collectively, these data indicate that this swell-activated adipocyte chloride current is VRAC or VSOR, as identified previously in other cell types, including adipocytes.

SWELL1/LRRC8a is Required for Swell-Activated VRAC in Adipocytes

Whether SWELL1 was required for adipocyte VRAC was next investigated. An adenovirus expressing a short-hairpin RNA directed to SWELL1 mRNA (Ad-shSWELL1-mCherry) was generated to knock-down SWELL1 in both mature, primary adipocytes and in adipocyte cell lines, while a scrambled shRNA served as a control (Ad-shSCR-mCherry). Robust knock-down (KD) of SWELL1 mRNA and protein was confirmed in cultured human pre-adipocytes upon adenoviral shRNA transduction. To knock-down SWELL1 in mature, primary murine adipocytes, Ad-shSWELL1/shSCR-mCherry was injected directly into iWAT of mice and then isolated and recorded from patch-clamped mCherry positive adipocytes 5 days later. ShRNA-mediated SWELL1 knock-down nearly abolished all swell-activated VRAC in murine adipocytes as compared to the scrambled shRNA control, in addition to VRAC in both murine 3T3-F442A adipocytes and in a human adipocyte cell line.

As a complementary approach, CRISPR/cas9 gene editing was used to disrupt SWELL1 using either a single guide RNA (gRNA) or double gRNA approach in the 3T3-F442A adipocyte line. From two independent SWELL1 CRISPR/cas9 knock-out (KO) adipocyte cell lines, it was found that VRAC is entirely abolished upon SWELL1 gene disruption, and this is associated with complete loss of SWELL1 protein.

To achieve conditional ablation of SWELL1, mice were generated with flanking loxP sites around SWELL1 Exon 3 (representing 90% of SWELL1 protein sequence, SWELL1$^{fl}$) by applying a CRISPR/cas9 knock-in approach to d0.5 mouse embryos. Cultured tail-tip fibroblasts from SWELL1$^{fl}$ mice transduced with adenoviral-Cre-mCherry (Ad-Cre-mCherry) show excision of SWELL1 Exon 3. Primary adipocytes isolated and cultured from the stromal vascular fraction (SVF) also show specific SWELL1 mRNA ablation when transduced (>90% efficient) with Ad-Cre-mCherry, and this is associated with ablation of VRAC. Next, VRAC was measured in mature murine adipocytes isolated from iWAT of SWELL1$^{fl}$ mice 5-7 days after direct injection with either Ad-mCherry or Ad-Cre-mCherry. SWELL1 deletion (Ad-Cre-mCherry) entirely ablates swell-induced VRAC in freshly isolated mature iWAT adipocytes. Collectively, these data show that SWELL1/LRRC8a is required for swell-induced VRAC currents in both primary adipocytes and adipocyte cell lines.

SWELL1-Mediated VRAC is Increased in Adipocytes of Obese Mice and Humans

Although studied for nearly 20 years prior to its molecular identification, VRAC has been largely measured in the context of hypotonic cell swelling and, accordingly, its primary function is thought to be cytoplasmic volume regulation. As adipocytes are not typically exposed to hypotonic interstitial fluid and resultant changes in ionic strength, osmolarity or cytoplasmic volume, it was hypothesized that SWELL1-LRRC8 complexes must function differently in adipocytes. Whether adipocyte hypertrophy arising from lipid droplet expansion in the setting of obesity could activate SWELL1-mediated VRAC at the adipocyte plasma membrane was investigated. Mature adipocytes were isolated from iWAT of lean (normal chow: NC, 10-12 weeks) and obese (high fat diet, HFD, 10-12 weeks) mice and measured VRAC using the perforated-patch configuration of the patch-clamp technique. This approach minimally perturbs the adipocyte plasma membrane, protects against lipid occluding the patch-pipette during recordings, and permits controlled activation of SWELL1-mediated current (via hypotonic swelling) which allows for more accurate quantification than can be achieved using positive-pressure induced adipocyte swelling in whole-cell configuration. Similar to positive-pressure adipocyte swelling, a minimal amount of adipocyte swelling is required (~1-2% increase in diameter) to activate robust SWELL1-LRRC8 mediated in adipocyte currents, which is easily within the physiological range of adipocyte expansion/contraction occurring during feeding/fasting. As expected, adipocytes isolated from obese mice are hypertrophic compared to lean mice based on cell size and cell capacitance, the latter providing a measure of adipocyte surface area. SWELL1-mediated current densities in hypertrophic adipocytes are significantly increased compared to adipocytes of lean mice, both upon adipocyte swelling and, importantly, prior to swelling. To determine whether these increases in SWELL1-mediated currents measured in hypertrophic adipocytes result from SWELL1-LRRC8 channel activation versus augmented SWELL1-LRRC8 channel expression, qPCR was performed to measure relative mRNA expression levels of SWELL1/LRRC8a, LRRC8b, LRRC8c, LRRC8d and LRRC8e in adipocytes from lean compared to obese mice, and a non-statistically significant trend toward increasing SWELL1 (2.2-fold; p=0.07) expression, with significant increases in LRRC8b (3-fold, p<0.05) and LRRC8d (2.9-fold, p<0.01) was found. Thus, it is possible that increases in adipocyte VRAC currents in obesity occur due to SWELL1-LRRC8 channel activation by adipocyte hypertrophy in addition to coordinated increases in SWELL1/LRRC8a, LRRC8b and LRRC8d expression.

Whether VRAC is also activated in hypertrophic adipocytes of obese humans and patch-clamped mature adipocytes freshly dissociated from visceral fat harvested from obese, BMI>30, bariatric surgery patients compared to leaner non-bariatric patients, BMI<30 was investigated. As in mice, there is a significant, though less marked, increase in adipocyte size and adipocyte capacitance in obese compared to leaner non-bariatric patients. Similarly, VRAC is augmented upon swelling in adipocytes from obese compared to leaner patients, as is basal or "pre-activated" VRAC inward current. Taken together, these data strongly suggest that SWELL1-mediated VRAC is augmented in adipocytes as they hypertrophy in obese mice and humans.

SWELL1 Regulates Lipid Content and Glucose Metabolism in 3T3-F442A Adipocytes

How SWELL1 loss-of function might impact adipocyte function was investigated. Genome-wide RNA sequencing (RNA Seq) of wild-type (WT) and CRISPR/cas9 mediated SWELL1 KO 3T3-F442A adipocytes reveal significant differences in RNA transcriptional profile with 9090 differentially expressed genes based on a false-discovery rate q-value of 0.25. To obtain unbiased insight into putative SWELL1-dependent molecular pathways, Gene Set Enrichment Analysis (GSEA) was performed of the RNA sequencing data. GSEA highlight pathways related to hypoxia, adipogenesis, glucose metabolism and insulin signaling. Consistent with a requirement for SWELL1 in adipogenesis, both SWELL1 KO 3T3-F442A adipocytes and cultured SWELL1 KO primary adipocytes develop less intracellular lipid than WT as assessed by AdipoRed fluorescence imaging (under high glucose culture conditions, 25 mM). Switching to low glucose media (5 mM) abolishes this difference in intracellular lipid content between WT and SWELL1 KO 3T3-F442A adipocytes. These data suggest that impaired glucose uptake, and consequently diminished de novo lipogenesis, underlies the reduction in lipid content in SWELL1 KO adipocytes relative to WT under high glucose culture conditions.

To investigate the putative role of SWELL1 in glucose uptake, basal and insulin-stimulated glucose uptake was measured in WT and SWELL1 KO 3T3-F442A adipocytes using radioactively labeled 2-deoxy-D-glucose. WT adipocytes exhibit the expected increase in glucose uptake upon insulin-stimulation, while this effect is abrogated in SWELL1 KO adipocytes. Also consistent with impaired insulin-stimulated glucose uptake, transmission electron microscopy (TEM) images of SWELL1 KO 3T3-F442A adipocytes reveal a significant reduction in glycogen content compared to WT 3T3-F442A adipocytes under conditions of chronic insulin stimulation (i.e. differentiation media, 860 nM). Taken together, these data suggest that SWELL1 is required for both glucose uptake/metabolism and lipogenesis in adipocytes.

SWELL1 Regulates Insulin-PI3K-AKT Signaling, GLUT4 Translocation, GSK3β and FOXO1

As both glucose uptake and lipogenesis require intact insulin-phosphoinositol 3-kinase-AKT2 (insulin-PI3K-AKT2) signaling in adipocytes, the integrity of this pathway was examined in SWELL1 KO adipocytes. SWELL1 deletion in both SWELL1 KO 3T3-F442A adipocytes and SWELL1 KO primary adipocytes significantly reduced insulin-stimulated pAKT2 (pSerine474) when compared to their respective WT adipocytes, whereas pAKT1 (pSerine473) levels remained constitutively increased. To determine whether SWELL1 silencing in mature adipocytes in vivo also disrupts insulin-PI3K-AKT signaling, insulin-stimulated pAKT2 and pAKT1 in iWAT of mice 7 days after direct iWAT injection with Ad-shSCR-mCherry/Ad-shSWELL1-mCherry were examined. Paralleling the in vitro data, iWAT SWELL1 knock-down significantly dampened insulin-pAKT2 signaling without influencing insulin-mediated phosphorylation of AKT1.

Downstream AKT-substrates were examined to determine how these are altered in response to SWELL1 deletion in 3T3-F442A adipocytes. As insulin-PI3K-AKT2 stimulates glucose uptake via GLUT4 plasma membrane translocation, insulin-stimulated GLUT4 translocation was directly measured, using a surface biotinylation approach to pull-down the plasma membrane (PM) fraction, and then blotted for GLUT4 in the membrane versus cytosol. Caveolin-1 (Cav1) served as an internal control to confirm equal PM protein loading between insulin-stimulation conditions. Insulin-stimulated GLUT4 PM translocation is reduced in SWELL1 KO adipocytes, providing a molecular mechanism for the decrease in insulin-stimulated glucose uptake observed in SWELL1 KO adipocytes. It is well established that phosphorylation-mediated inhibition of the RabGAP AS160 (pThreonine642) is required for insulin-stimulated GLUT4 vesicle docking and fusion with the PM, and that this phosphorylation event is AKT2-specific and AKT1-independent. pAS160/AS160 was found to be reduced in SWELL1 KO adipocytes compared to WT, consistent with the observed reduction in insulin-PI3K-pAKT2-GLUT4 signaling.

Insulin-PI3K-AKT-mediated phosphorylation of Glycogen Synthase Kinase-3β (pGSK3β) inhibits GSK3β activity and subsequently dis-inhibits glycogen synthase, allowing glucose to be stored as glycogen. Insulin-stimulated pGSK3β/GSK3β and pGSK3β/β-actin (pSerine9) were found to be reduced in SWELL1 KO adipocytes, providing a molecular mechanism for the reduction in glycogen granules observed on EM. Thus, SWELL1-mediated pAKT2 signaling appears to coordinately regulate both glucose import via GLUT4 translocation and glycogen synthesis via GSK3β. The AKT-substrate FOXO1, a transcription factor that suppresses adipocyte differentiation when nuclear localized, but upon insulin-AKT-mediated phosphorylation pFOXO1 becomes excluded from the nucleus—thereby releasing adipocyte differentiation programs, was examined. Insulin-AKT-mediated pFOXO1/FOXO1 and pFOXO1/β-actin (pThreonine24), are enhanced in SWELL1 KO adipocytes, in a manner similar to pAKT1. Taken together, these data show that SWELL1 is required for insulin-PI3K-AKT2 activity and downstream signaling in adipocytes and suggest that SWELL1 may connect volume of the expanding adipocyte with "tuning" of insulin-PI3K-AKT2 signaling. How then can this volume-sensitive protein modulate insulin-PI3K-AKT2 signaling in adipocytes?

SWELL1 Regulates Insulin-pAKT2 Signaling via GRB2-Dependent Interactions

In lymphocytes, SWELL1 connects with PI3K signaling via a Growth Factor Receptor-bound 2 (GRB2) interaction. GRB2 is linked to insulin receptor (IR) signaling via a direct interaction with insulin-receptor substrate (IRS) 1/2 and is thought to modulate insulin signaling. GRB2-IRS1-IR and SWELL1-GRB2 molecular interactions were examined to provide a molecular mechanism for the observed effects of SWELL1 deletion on insulin-PI3K-AKT2 signaling. First, it was confirmed that GRB2 co-immuno-precipitates (IP) with IR in both 3T3-F442A adipocytes and HEK cells. Second, it was confirmed that GRB2 co-IPs with IRS1 using an epitope-tagged IRS1 construct (Myc-TEV-HA-IRS1) expressed in HEK cells. Endogenous GRB2-SWELL1 interaction in adipocytes was investigated. It was found that GRB2 co-IPs with SWELL1 in WT but not SWELL1 KO 3T3-F442A adipocytes, and that insulin-stimulation reduces this SWELL1-GRB2 interaction, suggesting a dynamic, insulin-dependent SWELL1-GRB2 interaction.

GRB2 has also been reported to associate with caveolin-1 (Cav1). Cav1 is enriched in adipocytes, thought to form insulin signaling microdomains, is required for normal adipocyte insulin signaling and has been described as a cellular mechanosensor that regulates PI3K-AKT signaling. Moreover, there are reports that Cav1 regulates VRAC, further suggesting a putative SWELL1-Cav1 molecular interaction. It was found that Cav1 co-IPs with GRB2 in 3T3-F442 adipocytes, and SWELL1 also co-IPs with Cav1 in WT but not in SWELL1 KO 3T3-F442A adipocytes. These data suggest that SWELL1 resides in an insulin signaling macromolecular complex that includes Cav1, GRB2, IRS-1, and IR.

The region(s) of SWELL1 that interact with GRB2 were investigated. To determine if SWELL1 Leucine-Rich Repeat Domain (LRRD) is required for GRB2 binding, wild-type SWELL1, and the SWELL1 mutant, SWELL1$^{\Delta 91/+35}$ were expressed, in HEK cells and attempted to pull-down these SWELL1 proteins with endogenous GRB2. SWELL1$^{\Delta 91/+35}$ is a mutation identified in a patient with agammaglobulinemia which replaces 91 C-terminal LRRD amino acids with 35 amino acids derived from the neighboring intronic sequence; this partially disrupts the LRRD, and inactivates SWELL1 activity. When WT SWELL1 and SWELL1$^{\Delta 91/+35}$ are transiently expressed at equal levels in HEK cells (SWELL1/β-actin=1.38; SWELL1$^{\Delta 91/+35}$/β-actin=1.41) SWELL1$^{\Delta 91/+35}$ co-IP's with GRB2 less efficiently (SWELL1$^{\Delta 91/+35}$/GRB2=0.07) than WT SWELL1 (SWELL1/GRB2=0.31), suggesting that the SWELL1-LRRD is required for GRB2 binding.

How a SWELL1-GRB2 complex may regulate insulin signaling was investigated. It was found that insulin-stimulation reduces both SWELL1-GRB2 and Cav1-GRB2, but not SWELL1-Cav1 interactions in WT 3T3-F442A adipocytes, suggesting that insulin-stimulation induces GRB2 dissociation from the insulin-signaling complex, thereby dis-inhibiting downstream insulin signaling. Moreover, this insulin-mediated GRB2 dissociation from Cav1 is abrogated upon SWELL1 ablation, implying that SWELL1 may tune insulin signaling by titrating GRB2-interactions with components of the insulin signaling complex. To examine whether the defect in insulin-pAKT2 signaling observed upon SWELL1 KO is due to unrestrained GRB2-mediated inhibition, stable WT/GRB2 KD and SWELL1 KO/GRB2 KD 3T3-F442A adipocytes were generated using a lentiviral shRNA to GRB2. Enhanced insulin-pAKT2 signaling was observed in WT GRB2-deficient adipocytes, even under non-insulin stimulated conditions. Importantly, GRB2 KD in SWELL1 KO adipocytes rescues the impairment in insulin-pAKT2 activation, confirming that suppression of insulin-pAKT2 signaling upon SWELL1 ablation is GRB2-dependent. Overall, these data suggest that SWELL1 modulates insulin-PI3K-AKT2 signaling by titrating GRB2-inhibition of a Cav1-IRS1-IR signaling complex via a C-terminal LRRD-mediated interaction with GRB2.

SWELL1 Knock-Down Reduces Adipocyte Size, Adiposity and Impairs Glucose Tolerance in Obese Mice Based on the findings that SWELL1 is required for insulin-PI3K-AKT2 signaling and that SWELL1 is activated in hypertrophic adipocytes in the context of obesity, whether SWELL1 knock-down can influence adipocyte size, adiposity and glucose tolerance in obese mice was investigated. To test the acute effects of SWELL1 knock-down on adipocyte size, iWAT of obese mice (HFD, 10-12 weeks) was injected with either Ad-shSCR-mCherry or Ad-shSWELL1-mCherry and isolated and measured Ad-shSWELL1-mCherry and Ad-shSCR-mCherry transduced adipocytes after 12 days. Upon SWELL1 knock-down, SWELL1-depleted adipocytes are 28% smaller than control adipocytes with a leftward shifted size distribution. To examine the effects of long-term SWELL1 knock-down in vivo during the development of diet-induced obesity, adeno-associated viruses (AAV) were generated using a novel engineered hybrid capsid serotype (Rec2) for sustained viral expression of shSWELL1, as this AAV/Rec2 serotype has a very high tropism for adipose tissue and can sustain expression for up to 12 months. After direct iWAT injection with either AAV/Rec2-shSWELL1-mCherry or AAV/Rec2-shSCR-mCherry, both groups of mice were placed on a HFD for 16 weeks prior to analysis. Patch-clamp recordings from hypertrophic AAV/Rec2-shSWELL1-mCherry transduced iWAT adipocytes confirm strong SWELL1 silencing compared to AAV/Rec2-shSCR-mCherry at 16 weeks post injection and this is associated with reduced adipocyte size, as observed with acute adenoviral SWELL1 knock-down in iWAT of obese mice. Interestingly, while AAV/Rec2 iWAT transduction is patchy and restricted to the injection site, wide-spread viral transduction of much of the visceral adipose depot, in particular the epididymal white adipose tissue, was found. In addition, transduction of liver and skeletal muscle was observed, resulting in a pattern of AAV/Rec2 transduction, involving several insulin-sensitive tissues. Nuclear Magnetic Resonance (NMR) measurements reveal a trend toward reduction in total % fat in HFD mice treated with AAV/Rec2-shSWELL1-mCherry compared to AAV/Rec2-shSCR-mCherry, accompanied by a small increase in % lean mass. Based on the finding that visceral adipose was preferentially transduced by AAV/Rec2, it was hypothesized that much of the reduction in global adiposity measured by NMR might arise predominantly from contraction of the visceral depot. To discriminate subcutaneous from visceral adipose tissue non-invasively in vivo, microCT imaging was used to provide accurate anatomic volumetric quantification of adipose tissue with micrometer spatial resolution. MicroCT imaging revealed a significant reduction in visceral adiposity as opposed to subcutaneous, and in particular the epididymal fat depot, consistent with preferential SWELL1 KD in visceral fat. Both glucose and insulin tolerance were examined in AAV/Rec2-shSCR-mCherry and AAV/Rec2-shSWELL1-mCherry mice raised on a HFD. Consistent with our findings in cultured cells, SWELL1 knock down in vivo is associated with impaired glucose tolerance and insulin resistance.

Adipocyte-Restricted SWELL1 Deletion Induces Systemic Glucose Intolerance and Insulin-Resistance As a complementary approach to the AAV/Rec2-mediated SWELL1 KD experiments, adipose-targeted SWELL1 knock-out (Adipo KO) mice were generated by crossing SWELL1 mice with Adiponectin-Cre mice to achieve adipose-restricted Cre-mediated SWELL1 recombination using the Cre-loxP system. Adipo KO mice showed clear adipose-restricted SWELL1 Exon 3 deletion in subcutaneous (iWAT), visceral (eWAT) and brown (BAT) adipose tissue without evidence of recombination in other tissues. SWELL1-LRRC8 currents were entirely ablated in mature Adipo KO adipocytes compared to WT adipocytes. At baseline, Adipo KO mice were indistinguishable from littermate SWELL1$^{fl}$ controls (WT, age and gender matched) with respect to total body weight and adiposity—as assessed by both NMR and iWAT/eWAT weights. Moreover, there were no differences in adipocyte size. mRNA expression levels of adipocyte differentiation markers, including Adiponectin, C/EBPα, C/EBPIβ, and PPARγ were either unchanged or slightly increased in iWAT of Adipo KO mice compared to WT. Despite normal adipocyte development, Adipo KO mice exhibited impaired glucose tolerance and insulin-sensitivity compared to WT, as observed with systemic AAV/Rec2-mediated SWELL1 knock down. Collectively, these data indicate that adipocyte SWELL1 is required for normal systemic glycemia and insulin-sensitivity but is dispensable for normal postnatal development and differentiation of adipocytes in vivo under basal conditions.

Adipocyte-Restricted SWELL1 Ablation Limits Adiposity and Adipocyte Size in Obese Mice As SWELL1-LRRC8 activity is augmented in the setting of obesity in mice and humans, whether SWELL1 is required for adipocyte hypertrophy under conditions of over-nutrition were investigated. Adipo KO mice placed on a HFD (16 weeks) gained less weight, despite no consistent differences in daily food consumption, and this is attributed to a marked reduction in percent adiposity and total adipose mass; while percent lean mass is proportionately increased, with total lean mass unchanged. Dissection of inguinal and epididymal fat pads also revealed marked differences in size and weight of iWAT and eWAT in Adipo KO mice relative to WT littermate controls.

As the reduction in total adiposity and fat pad size observed in Adipo KO mice may arise from fewer adipocytes, smaller adipocytes, or both, adipocyte size in WT and Adipo KO mice was measured. Measurements of adipocyte cross-sectional areas from H&E stained sections of HFD Adipo KO and WT iWAT revealed a striking reduction in adipocyte size in Adipo KO mice relative to WT. Overlaying the adipocyte size distribution of lean/obese, WT and Adipo KO mice showed that SWELL1 deletion has no effect on adipocyte size in lean mice but induces a clear leftward shift in adipocyte size in the setting of obesity toward a lean phenotype. Adipocyte size of freshly dissociated adipocytes isolated from HFD Adipo KO iWAT were also significantly smaller than WT, with a leftward shifted size distribution; comparable in relative size reduction to viral knock-down studies. Moreover, glucose intolerance and insulin-resistance associated with obesity was further exacerbated in Adipo KO mice compared to WT littermates controls.

To determine whether these differences in adiposity and adipocyte size in Adipo KO relative to WT mice are related to differences in energy expenditure, heat production, $VO_2$, $VCO_2$, RER, food consumption, activity level and sleep in both lean and obese mice were measured by indirect calorimetry. There were no differences in any measured parameter in lean WT compared to Adipo KO mice. In obese mice, an increase in energy expenditure in Adipo KO mice was observed, but this was associated with an increase in activity level, which may be driving the increased energy expenditure.

Collectively, these data identify SWELL1 as a swell-activated, volume-sensitive regulator of adipocyte growth, adiposity and insulin signaling and delineates a SWELL1/LRRD-GRB2-Cav1-IRS1-PI3K-AKT2 signaling pathway in adipocytes.

To summarize, the data presented herein show that the recently identified membrane protein, SWELL1, is a critical component of a prominent volume-sensitive ion channel in adipocytes that is activated in the context of adipocyte hypertrophy in obesity, and is required for adipocyte expansion and insulin-PI3K-AKT2 signaling via a LRRD-mediated GRB2 interaction. These findings link SWELL1 with adipocyte insulin-signaling and provide a putative molecular mechanism for the previously described effects of adipocyte membrane tension on lipogenesis and intracellular signaling. Proposed herein is a working model in which SWELL1 is activated by increases in adipocyte volume during adipocyte hypertrophy, and potentiates insulin-PI3K-AKT2 signaling via C-terminal LRRD interactions with GRB2-Cav1-IRS1-IR to support insulin-mediated GLUT4 PM translocation, glucose import and lipogenesis. In this model, SWELL1 senses adipocyte volumetric expansion and acts as a feed-forward amplifier to further promote adipocyte expansion, energy storage, and enhance insulin-AKT2 signaling during times of caloric excess (feeding).

It may be possible that SWELL1 Leucine-Rich Repeat Domains (LRRD) provides docking surfaces for protein-protein interactions, and passively promotes the association of components of the insulin signaling cascade (GRB2), or other signaling pathways. SWELL1 also forms heteromultimers with LRRC8b-e, which modifies channel gating, and may influence the diversity of molecular interactions with different protein partners based on the relative abundance of LRRC8b-e in a given cell type or tissue. Therefore, depending on the expression profile of LRRC8 proteins in different tissues, SWELL1 modulation of intracellular signaling may vary in a cell-type dependent fashion. For example, the broadly expressed membrane protein LRRC8c, also named Factor of Adipocyte Differentiation (FAD) 158, is identified as a novel factor required for adipocyte differentiation and diet-induced obesity—through un-identified molecular mechanisms. As LRRC8c (FAD158) forms a complex with SWELL1 and modifies SWELL1-LRRC8 channel function, these present findings may provide a mechanism for FAD158/LRRC8c action in adipocyte biology.

An intriguing observation is that adipose-targeted SWELL1 ablation appears not to grossly affect adipocyte development, adipocyte size or adiposity under basal conditions, but results in significant suppression of adipocyte expansion in the setting of obesity. This finding is in line with current observation that SWELL1 is activated in hypertrophic adipocytes from obese mice and humans, suggesting that SWELL1 activity is primarily required for extremes of adipocyte expansion in obese states. This phenotype is also consistent with the finding that SWELL1 deletion disrupts specifically PI3K-AKT2 signaling—an AKT isoform that is dispensable for adipocyte development, and instead is primarily important in "obesogenic" adipogenesis and systemic glucose homeostasis, in contrast to AKT1. Moreover, Adipo KO mice phenocopy $AKT2^{-/-}$ mice and adipose-targeted GLUT4 KO mice with respect to systemic glucose intolerance and insulin resistance, supporting the notion of a SWELL1-regulated insulin-AKT2-GLUT4 pathway.

The LRRD-mediated SWELL1-GRB2-Cav1 molecular interaction connecting SWELL1 to insulin-PI3K-AKT2 signaling is both consistent with the SWELL1(LRRC8a)-GRB2-GAB2-LCK complex reported in lymphocytes and also provides a molecular mechanism for the observed defect in insulin-PI3K-AKT2 signaling upon adipocyte SWELL1 ablation. Likewise, the SWELL1-Cav1 interaction is also compelling as this positions SWELL1 within caveolae, which are abundant in adipocytes, are thought to form insulin-signaling microdomains and are required for normal insulin and PI3K-AKT[43] signaling. Indeed, Cav1 KO mice on a HFD are phenotypically similar to adipose-targeted SWELL1 KO mice with respect to adiposity, adipocyte size, and insulin-sensitivity.

Accordingly, it has been described herein that SWELL1 is a required component of a volume-sensitive ion channel complex that is activated in the setting of obesity and positively regulates adipocyte lipid content and glucose uptake via GRB2-mediated modulation of insulin-PI3K-AKT2 signaling. Certain aspects of the discoveries are also presented in Zhang et al., *Nature Cell Biology* (2017) doi:10.1038/ncb3514, the full disclosure of which, including Supplementary Information, is specifically incorporated by reference.

Example 2

SWELL1 is a Glucose Sensor Required for β-Cell Excitability and Insulin Secretion Recent studies have identified SWELL1 (LRRC8a) as a required component of a swell-activated Cl⁻ current $I_{Cl,SWELL}$ or Volume-Regulated Anion Current (VRAC) in common cell lines, forming multimeric channels with LRRC8b-e. To determine if SWELL1 is also required for VRAC in pancreatic β-cells, SWELL1 was suppressed in mouse insulinoma (MIN6) cells by adenoviral transduction with an shRNA-directed against SWELL1 (Ad-U6-shSWELL1-mCherry) as compared to a scrambled shRNA control (Ad-U6-shSCR-mCherry). Robust knock-down of SWELL1 protein was observed, and a significant reduction in hypotonic swell-activated VRAC in Ad-shSWELL1 relative to Ad-shSCR transduced MIN6 cells was observed. To determine whether SWELL1 is also required for VRAC in mouse primary β-cells, islets were isolated from SWELL1 foxed mice (SWELL1$^{fl}$) and transduced with an adenovirus expressing GFP under control of a rat insulin promoter (Ad-RIP2-GFP) to allow positive identification of β-cells (GFP+ cells). SWELL1$^{fl}$ islets were further treated with adenovirus expressing Cre-mCherry to allow Cre-mediated excision of the floxed SWELL1 allele or control virus expressing mCherry alone. By selecting GFP+/mCherry+ cells, it was possible to patch-clamp either control WT β-cells (SWELL1$^{fl}$ β-cells) or SWELL1 KO β-cells (SWELL1$^{fl/fl}$/Cre β-cells. WT β-cells expressed substantial swell-activated current and this is entirely abolished upon Cre-mediated recombination in SWELL1 KO β-cells. Whether SWELL1 is also required for VRAC in human β-cells was also investigated using a similar approach. Human islets were transduced with Ad-RIP2-GFP and Ad-shSWELL1-mCherry or Ad-sh-SCR-mCherry, in order to isolate and patch-clamp human β-cells (GFP+) subjected to shRNA-mediated SWELL1 KD or to a scrambled control (GFP+/mCherry+. Similar to mouse β-cell recordings, human β-cells also express significant SWELL1-mediated swell-activated current. Indeed, in all β-cells patch-clamped, the reversal potential was ~−12 mV, which is near the reversal potential for Cl⁻ under our recording conditions, and thus consistent with SWELL1-mediating a swell-activated Cl⁻ conductance in β-cells. These data demonstrate that SWELL1 is required for VRAC or I$_{Cl,SWELL}$ in pancreatic β-cells.

Having established that SWELL1 is required for this previously enigmatic depolarizing swell-activated Cl⁻ current in MIN6 cells, and in both mouse and human primary β-cells, whether physiologic glucose-mediated β-cell swelling is sufficient to activate SWELL1-mediated VRAC was investigated. First, β-cell size was measured by light microscopy in WT and SWELL1-deficient primary murine and human β-cells in response to glucose-stimulated swelling (at 35-37° C.). WT murine β-cells swell 6.8±1.6% in cross-sectional area upon perfusion of 16.7 mM glucose (from 1 mM basal glucose) and reach a maximum size at 12 minutes post glucose-stimulation, followed by a reduction in β-cell size, consistent with regulatory volume decrease (RVD). In contrast, SWELL1 KO murine β-cells swell monotonically to 8.2±2.4% and exhibit no RVD. WT human β-cells show a similar trend, swelling 8.6±3.5%, followed by RVD. SWELL1 KD human β-cells swell monotonically to 6.0±1.5%, and similar to SWELL1 KO murine β-cells, exhibit no RVD. These data indicate that physiological increases in glucose induce β-cell swelling and that SWELL1 is required for RVD in primary β-cells. Next, the perforated-patch clamp technique was applied to primary β-cells at 35-37° C. in order to measure currents under the same physiological conditions that induce glucose-mediated β-cell swelling. β-cell VRAC activates in response to physiological increases in glucose in MIN6 cells and in both mouse and human β-cells, and is blocked by the selective VRAC inhibitor, DCPIB. Importantly, the time-course of VRAC activation in β-cells either tracks or lags the latency of β-cell swelling in response to stimulatory glucose (~8 minutes), consistent with a mechanism of glucose-mediated β-cell swell-activation of SWELL1-mediated VRAC. Thus, SWELL1-mediates a glucose-sensitive swell-activated depolarizing Cl⁻ current in β-cells.

To determine whether SWELL1-mediated depolarizing Cl⁻ current is required to depolarize the β-cell membrane potential to the activation threshold of voltage-gated Ca$^{2+}$ channels (VGCC) essential for insulin granule fusion, glucose-stimulated intracellular Ca$^{2+}$ was measured in WT and SWELL1-deficient MIN6 β-cells, primary mouse and human β-cells. Using CRISPR/cas9 technology, multiple SWELL1 KO MIN6 cell lines were generated, and confirmed ablation of SWELL1 protein and SWELL1-mediated current was demonstrated in these cells. Glucose-stimulated Ca$^{2+}$ transients are entirely abolished in SWELL1 KO MIN6 compared to WT cells, despite preserved KCl (40 mM) stimulated Ca$^{2+}$ transients (control for intact β-cell excitability). Co-application of a selective VGCC blocker nifedipine (10 μM) fully inhibits these glucose-stimulated Ca$^{2+}$ transients in WT MIN6 cells, consistent with a mechanism of membrane depolarization and VGCC activation.

As β-cells also depolarize, fire Ca$^{2+}$ transients, and secrete insulin via a glucose-independent hypotonic swelling mechanism, swell-induced Ca$^{2+}$-signaling was examined in β-cells in response to hypotonic stimulation (220 mOsm) in the absence of glucose-stimulation (0 mM glucose). Hypotonic swelling alone was found trigger robust Ca$^{2+}$ transients in WT MIN6 cells and these elevations in cytosolic Ca$^{2+}$ recover rapidly upon restoration of isotonic solution. In contrast, SWELL1 KO MIN6 cells are entirely non-responsive to hypotonic swelling induced Ca$^{2+}$ transients, despite preserved KCl stimulated Ca$^{2+}$ responses, consistent with SWELL1-mediating a glucose-independent, swell-activated depolarizing current in β-cells. Similar to the case with glucose-stimulated Ca$^{2+}$ signaling, hypotonic swelling triggered Ca$^{2+}$ transients are fully inhibited by VGCC blockade, implicating β-cell membrane depolarization followed by VGCC activation, as opposed to alternative hypo-osmotically activated Ca$^{2+}$ influx pathways (i.e. TRP channels).

SWELL1-dependent Ca$^{2+}$ signaling was then examined in primary mouse and human β-cells. Adenoviruses expressing the genetically encoded Ca$^{2+}$-sensor GCaMP6s under control of the rat insulin promoter 1 (RIP1), either alone (Ad-RIP1-GCaMP6s), or in combination with Cre-recombinase (Ad-RIP1-Cre-P2A-GCaMP6s), were generated. This approach provides a robust β-cell restricted fluorescent Ca$^{2+}$ sensor while simultaneously allowing for β-cell targeted Cre-mediated SWELL1 deletion in cultured SWELL1$^{fl/fl}$ islets isolated from SWELL1$^{fl/fl}$ mice. GCaMP6s Ca$^{2+}$ imaging revealed robust glucose-stimulated Ca$^{2+}$ transients in freshly dissociated WT primary murine β-cells (Ad-RIP1-GCaMP6s/SWELL1$^{fl/fl}$) and these are significantly suppressed in SWELL1 KO β-cells (Ad-RIP1-Cre-P2A-GCaMP6s/SWELL1$^{fl/fl}$), despite preserved KCl stimulated Ca$^{2+}$ responses. A similar approach was used in human islets, whereby islets were co-transduced with Ad-RIP1-GCaMP6s and either Ad-U6-shSWELL1-mCherry or Ad-U6-shSCR-mCherry. Upon islet dissociation, only double-labelled GCaMP6s+/mCherry+ primary human β-cells were imaged. As with mouse primary β-cells, robust glucose-stimulated Ca$^{2+}$ transients in Ad-shSCR treated human primary β-cells were observe, and this is markedly aborgated upon Ad-shSWELL1-mediated SWELL1 knock-down. Collectively, these data demonstrate that SWELL1 is required for both glucose- and swell-activated Ca$^{2+}$ signaling in MIN6 cells and in mouse and human primary β-cells. Moreover, these data suggest that the depolarizing SWELL1-mediated Cl⁻ current is necessary for β-cell depolarization in response to glucose-stimulation. In pancreatic β-cells, physiological intracellular Cl⁻ concentration is maintained at 34-36 mM by NKCC1 transporters to generate a depolarizing Cl⁻ current upon activation of a Cl⁻ conductance, since $E_{Cl^-}=\sim-35$ mV. Therefore, NKCC1 blockade by bumetanide is predicted to reduce intracellular Cl⁻, drop $E_{Cl^-}$ and thereby diminish or abolish β-cell membrane depolarization by a SWELL1-mediated glucose-stimulated Cl⁻ conductance. Consistent with this prediction, bumetanide (10 μM) application fully inhibits glucose-stimulated $Ca^{2+}$ signaling in both WT MIN6 cells and WT primary murine β-cells.

To determine the impact of SWELL1-dependent glucose-stimulated $Ca^{2+}$ signaling on insulin secretion in β-cells, glucose-stimulated insulin secretion (GSIS) was measured in WT and SWELL1 KO MIN6 cells. Glucose-dependent increase in insulin secretion in WT MIN6 cells is significantly diminished in SWELL1 KO MIN6 cells, particularly at higher glucose concentration (30 mM), despite no change in total insulin content. Iislets from SWELL1$^{fl/fl}$ mice were isolated followed by transduction with either Ad-RIP1-RFP (WT) or Ad-RIP1-Cre-P2A-RFP (SWELL1 KO. Similar to MIN6 cells, a significant reduction in GSIS (16.7 mM glucose) was found in SWELL1 KO compared to WT islets, despite relatively preserved L-arginine stimulated insulin secretion, and similar total insulin content. These data are consistent with a requirement of β-cell SWELL1 for $Ca^{2+}$-dependent insulin vesicle fusion and insulin secretion.

VRAC/$I_{Cl,SWELL}$ has been studied for decades through electrophysiological recordings in numerous cell types, but only recently has it been discovered that SWELL1/LRRC8a, and associated LRRC8 isoforms b-e, form the VRAC channel complex in common cell lines. Here it was asked whether SWELL1 is required for VRAC described previously in the pancreatic β-cell and whether the VRAC hypothesis can be explained by a putative glucose-mediated swell sensing function of the SWELL1/LRRC8 channel complex in β-cells. Indeed, this data are consistent with a model in which SWELL1 is a required component of a swell-activated depolarizing Cl⁻ channel that activates in response to glucose-stimulated β-cell swelling and is required for membrane depolarization, VGCC activation, $Ca^{2+}$-mediated insulin vesicle fusion and insulin secretion. In this model, the hyperpolarizing K⁺ conductances act as a "brakes" on β-cell excitability and insulin secretion, while SWELL1-mediated VRAC is the "accelerator"—promoting β-cell excitability in response to glucose-mediated β-cell swelling. Overall, these data suggest that SWELL1 acts as a glucose sensor by coupling β-cell swelling to β-cell depolarization—a form of swell-activation or swell-secretion coupling—to potentiate glucose-stimulated insulin secretion.

All documents cited herein are incorporated by reference. While certain embodiments of invention are described, and many details have been set forth for purposes of illustration, certain of the details can be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not necessarily impose a limitation on the scope of the invention unless otherwise specifically recited in the claims. No language in the specification should be construed as indicating that any non-claimed element is essential to the practice of the invention.

What is claimed is:

1. A method for treating type 2 diabetes in a human patient in need of such treatment, comprising administering to the patient a therapeutically effective amount of a SWELL1 modulator, wherein the SWELL1 modulator is a compound of formula I:

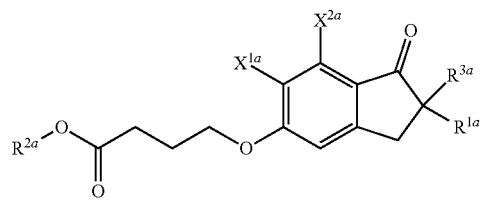

wherein:
 $X^{1a}$ and $X^{2a}$ are independently halogen;
 $R^{1a}$ is $C_{1-6}$ alkyl, 3-6 membered cycloalkyl, or phenyl, wherein the $C_{1-6}$ alkyl is optionally substituted with 3-6 membered cycloalkyl;
 $R^{2a}$ is hydrogen or $C_{1-6}$ alkyl, wherein the $C_{1-6}$ alkyl is optionally substituted with carboxy; and
 $R^{3a}$ is $C_{1-6}$ alkyl;
or a pharmaceutically acceptable salt thereof.

2. The method of claim 1, wherein the SWELL1 modulator is DCPIB.

3. The method of claim 1, wherein the administering to the patient of the SWELL1 modulator is sufficient to upregulate the expression of SWELL1, or alter expression of a SWELL1 associated protein.

4. The method of claim 1, wherein the administering to the patient of the SWELL1 modulator is sufficient to upregulate the expression of SWELL1.

5. The method of claim 3, wherein the SWELL1 associated protein is LRRC8b,c,d,e, GRB2, Cav1, IRS1, or IRS2.

6. The method of claim 1, wherein the administering to the patient of the therapeutically effective amount of the SWELL1 modulator increases the patient's insulin sensitivity.

7. The method of claim 1, wherein the administering to the patient of the therapeutically effective amount of the SWELL1 modulator increases the patient's insulin secretion.

* * * * *